(12) United States Patent
Guerrera et al.

(10) Patent No.: US 11,723,664 B2
(45) Date of Patent: Aug. 15, 2023

(54) PROGRAMMABLE DISTAL TILT POSITION OF END EFFECTOR FOR POWERED SURGICAL DEVICES

(71) Applicant: Covidien LP, Mansfield, MA (US)

(72) Inventors: Joseph Guerrera, Watertown, CT (US); Steven H. Joyce, Durham, CT (US)

(73) Assignee: Covidien LP, Mansfield, MA (US)

( * ) Notice: Subject to any disclaimer, the term of this patent is extended or adjusted under 35 U.S.C. 154(b) by 0 days.

(21) Appl. No.: 17/552,746

(22) Filed: Dec. 16, 2021

(65) Prior Publication Data

US 2022/0104824 A1 Apr. 7, 2022

Related U.S. Application Data

(63) Continuation of application No. 16/732,620, filed on Jan. 2, 2020, now Pat. No. 11,202,635.
(Continued)

(51) Int. Cl.
*A61B 17/064* (2006.01)
*A61B 17/115* (2006.01)
(Continued)

(52) U.S. Cl.
CPC ......... *A61B 17/1155* (2013.01); *A61B 17/295* (2013.01); *A61B 2017/0053* (2013.01);
(Continued)

(58) Field of Classification Search
CPC ........................................... A61B 2017/00398
(Continued)

(56) References Cited

U.S. PATENT DOCUMENTS

| 37,165 A | 12/1862 | Gary |
| 3,209,754 A | 10/1965 | Brown |

(Continued)

FOREIGN PATENT DOCUMENTS

| CN | 101683284 A | 3/2010 |
| CN | 102648864 A | 8/2012 |

(Continued)

OTHER PUBLICATIONS

Extended European Search Report dated Sep. 12, 2022 issued in corresponding EP Appln. No. 22168882.3.
(Continued)

*Primary Examiner* — Eyamindae C Jallow
(74) *Attorney, Agent, or Firm* — Carter, DeLuca & Farrell LLP

(57) ABSTRACT

A surgical device includes a handle assembly having a controller and a motor. The surgical device also includes an adapter assembly having: a tubular housing having a proximal end portion configured to couple to the handle assembly and a distal end portion; and an actuation assembly configured to couple to the motor. The surgical further includes a reload configured to couple to the distal end portion of the adapter assembly; and an anvil assembly including an anvil head pivotally coupled to an anvil shaft, the anvil assembly configured to couple to the actuation assembly and the reload. The controller of the surgical device is configured to control the motor to actuate the actuation assembly to move the anvil assembly in a distal direction for a distance based on a dimension of one of the reload or the anvil head, thereby pivoting the anvil head relative to the anvil shaft while maintaining engagement of the anvil assembly to the reload.

10 Claims, 11 Drawing Sheets

Related U.S. Application Data

(60) Provisional application No. 62/800,836, filed on Feb. 4, 2019.

(51) Int. Cl.
*A61B 17/295* (2006.01)
*A61B 17/00* (2006.01)
*A61B 17/072* (2006.01)

(52) U.S. Cl.
CPC ............... *A61B 2017/00398* (2013.01); *A61B 2017/00486* (2013.01); *A61B 2017/07257* (2013.01); *A61B 2017/07285* (2013.01)

(58) Field of Classification Search
USPC ...................................................... 227/181.1
See application file for complete search history.

(56) References Cited

U.S. PATENT DOCUMENTS

| | | |
|---|---|---|
| 3,273,562 A | 9/1966 | Brown |
| 3,499,591 A | 3/1970 | Green |
| 3,528,693 A | 9/1970 | Pearson et al. |
| 3,744,495 A | 7/1973 | Johnson |
| 3,862,631 A | 1/1975 | Austin |
| 3,949,924 A | 4/1976 | Green |
| 4,060,089 A | 11/1977 | Noiles |
| 4,204,623 A | 5/1980 | Green |
| 4,217,902 A | 8/1980 | March |
| 4,263,903 A | 4/1981 | Griggs |
| 4,275,813 A | 6/1981 | Noiles |
| 4,331,277 A | 5/1982 | Green |
| 4,428,376 A | 1/1984 | Mericle |
| 4,429,695 A | 2/1984 | Green |
| 4,444,181 A | 4/1984 | Wevers et al. |
| 4,454,875 A | 6/1984 | Pratt et al. |
| 4,456,006 A | 6/1984 | Wevers et al. |
| 4,485,816 A | 12/1984 | Krumme |
| 4,485,817 A | 12/1984 | Swiggett |
| 4,488,523 A | 12/1984 | Shichman |
| 4,508,253 A | 4/1985 | Green |
| 4,508,523 A | 4/1985 | Leu |
| 4,522,206 A | 6/1985 | Whipple et al. |
| 4,534,350 A | 8/1985 | Golden et al. |
| 4,535,772 A | 8/1985 | Sheehan |
| 4,566,620 A | 1/1986 | Green et al. |
| 4,570,623 A | 2/1986 | Ellison et al. |
| 4,606,343 A | 8/1986 | Conta et al. |
| 4,606,344 A | 8/1986 | Di Giovanni |
| 4,610,383 A | 9/1986 | Rothfuss et al. |
| 4,612,923 A | 9/1986 | Kronenthal |
| 4,612,933 A | 9/1986 | Brinkerhoff et al. |
| D286,442 S | 10/1986 | Korthoff et al. |
| 4,627,437 A | 12/1986 | Bedi et al. |
| 4,635,637 A | 1/1987 | Schreiber |
| 4,662,371 A | 5/1987 | Whipple et al. |
| 4,671,280 A | 6/1987 | Dorband et al. |
| 4,705,038 A | 11/1987 | Sjostrom et al. |
| 4,712,550 A | 12/1987 | Sinnett |
| 4,719,917 A | 1/1988 | Barrows et al. |
| 4,724,839 A | 2/1988 | Bedi et al. |
| 4,731,058 A | 3/1988 | Doan |
| 4,805,617 A | 2/1989 | Bedi et al. |
| 4,807,628 A | 2/1989 | Peters et al. |
| 4,852,558 A | 8/1989 | Outerbridge |
| 4,913,144 A | 4/1990 | Del Medico |
| 4,960,420 A | 10/1990 | Goble et al. |
| 4,962,877 A | 10/1990 | Hervas |
| 4,990,153 A | 2/1991 | Richards |
| 4,994,073 A | 2/1991 | Green |
| 4,995,877 A | 2/1991 | Ams et al. |
| 5,040,715 A | 8/1991 | Green et al. |
| 5,065,929 A | 11/1991 | Schulze et al. |
| 5,089,009 A | 2/1992 | Green |
| 5,108,422 A | 4/1992 | Green et al. |
| 5,114,399 A | 5/1992 | Kovalcheck |
| 5,129,570 A | 7/1992 | Schulze et al. |
| 5,143,453 A | 9/1992 | Weynant nee Girones |
| 5,203,864 A | 4/1993 | Phillips |
| 5,207,697 A | 5/1993 | Carusillo et al. |
| 5,209,756 A | 5/1993 | Seedhom et al. |
| 5,246,443 A | 9/1993 | Mai |
| 5,258,008 A | 11/1993 | Wilk |
| 5,271,543 A | 12/1993 | Grant et al. |
| RE34,519 E | 1/1994 | Fox et al. |
| 5,282,829 A | 2/1994 | Hermes |
| 5,300,081 A | 4/1994 | Young et al. |
| 5,307,976 A | 5/1994 | Olson et al. |
| 5,312,023 A | 5/1994 | Green et al. |
| 5,312,024 A | 5/1994 | Grant et al. |
| 5,313,935 A | 5/1994 | Kortenbach et al. |
| 5,318,221 A | 6/1994 | Green et al. |
| 5,326,013 A | 7/1994 | Green et al. |
| 5,330,486 A | 7/1994 | Wilk |
| 5,332,142 A | 7/1994 | Robinson et al. |
| 5,342,376 A | 8/1994 | Ruff |
| 5,350,355 A | 9/1994 | Sklar |
| 5,356,064 A | 10/1994 | Green et al. |
| 5,359,993 A | 11/1994 | Slater et al. |
| 5,364,001 A | 11/1994 | Bryan |
| 5,381,943 A | 1/1995 | Allen et al. |
| 5,383,874 A | 1/1995 | Jackson et al. |
| 5,383,880 A | 1/1995 | Hooven |
| 5,389,098 A | 2/1995 | Tsuruta et al. |
| 5,391,166 A | 2/1995 | Eggers |
| 5,395,030 A | 3/1995 | Kuramoto et al. |
| 5,395,033 A | 3/1995 | Byrne et al. |
| 5,400,267 A | 3/1995 | Denen et al. |
| 5,403,312 A | 4/1995 | Yates et al. |
| 5,405,344 A | 4/1995 | Williamson et al. |
| 5,411,508 A | 5/1995 | Bessler et al. |
| 5,413,267 A | 5/1995 | Solyntjes et al. |
| 5,431,323 A | 7/1995 | Smith et al. |
| 5,464,144 A | 11/1995 | Guy et al. |
| 5,467,911 A | 11/1995 | Tsuruta et al. |
| 5,478,344 A | 12/1995 | Stone et al. |
| 5,482,100 A | 1/1996 | Kuhar |
| 5,485,947 A | 1/1996 | Olson et al. |
| 5,487,499 A | 1/1996 | Sorrentino et al. |
| 5,497,933 A | 3/1996 | DeFonzo et al. |
| 5,500,000 A | 3/1996 | Feagin et al. |
| 5,503,320 A | 4/1996 | Webster et al. |
| 5,507,743 A | 4/1996 | Edwards et al. |
| 5,518,163 A | 5/1996 | Hooven |
| 5,518,164 A | 5/1996 | Hooven |
| 5,526,822 A | 6/1996 | Burbank et al. |
| 5,529,235 A | 6/1996 | Boiarski et al. |
| 5,531,744 A | 7/1996 | Nardella et al. |
| 5,533,661 A | 7/1996 | Main et al. |
| 5,535,934 A | 7/1996 | Boiarski et al. |
| 5,535,937 A | 7/1996 | Boiarski et al. |
| 5,558,671 A | 9/1996 | Yates |
| 5,560,532 A | 10/1996 | DeFonzo et al. |
| 5,562,239 A | 10/1996 | Boiarski et al. |
| 5,571,285 A | 11/1996 | Chow et al. |
| 5,575,799 A | 11/1996 | Bolanos et al. |
| 5,582,611 A | 12/1996 | Tsuruta et al. |
| 5,584,835 A | 12/1996 | Greenfield |
| 5,601,224 A | 2/1997 | Bishop et al. |
| 5,601,558 A | 2/1997 | Forrie et al. |
| 5,607,095 A | 3/1997 | Smith et al. |
| 5,609,285 A | 3/1997 | Grant et al. |
| 5,609,560 A | 3/1997 | Ichikawa et al. |
| 5,624,452 A | 4/1997 | Yates |
| 5,632,433 A | 5/1997 | Grant et al. |
| 5,634,926 A | 6/1997 | Jobe |
| 5,642,848 A | 7/1997 | Ludwig et al. |
| 5,653,374 A | 8/1997 | Young et al. |
| 5,658,300 A | 8/1997 | Bito et al. |
| 5,658,312 A | 8/1997 | Green et al. |
| 5,662,662 A | 9/1997 | Bishop et al. |
| 5,665,085 A | 9/1997 | Nardella |
| 5,667,513 A | 9/1997 | Forrie et al. |
| 5,667,517 A | 9/1997 | Hooven |

(56) References Cited

U.S. PATENT DOCUMENTS

| | | |
|---|---|---|
| 5,667,527 A | 9/1997 | Cook |
| 5,669,544 A | 9/1997 | Schulze et al. |
| 5,673,841 A | 10/1997 | Schulze et al. |
| 5,676,674 A | 10/1997 | Bolanos et al. |
| 5,680,981 A | 10/1997 | Mililli et al. |
| 5,680,982 A | 10/1997 | Schulze et al. |
| 5,690,675 A | 11/1997 | Sawyer et al. |
| 5,692,668 A | 12/1997 | Schulze et al. |
| 5,695,506 A | 12/1997 | Pike et al. |
| 5,695,524 A | 12/1997 | Kelley et al. |
| 5,702,447 A | 12/1997 | Walch et al. |
| 5,704,534 A | 1/1998 | Huitema et al. |
| 5,713,505 A | 2/1998 | Huitema |
| 5,713,896 A | 2/1998 | Nardella |
| 5,715,987 A | 2/1998 | Kelley et al. |
| 5,716,366 A | 2/1998 | Yates |
| 5,720,753 A | 2/1998 | Sander et al. |
| 5,725,529 A | 3/1998 | Nicholson et al. |
| 5,728,110 A | 3/1998 | Vidal et al. |
| 5,728,116 A | 3/1998 | Rosenman |
| 5,730,757 A | 3/1998 | Benetti et al. |
| 5,735,848 A | 4/1998 | Yates et al. |
| 5,738,474 A | 4/1998 | Blewett |
| 5,755,726 A | 5/1998 | Pratt et al. |
| 5,759,171 A | 6/1998 | Coelho et al. |
| 5,779,130 A | 7/1998 | Mesi et al. |
| 5,782,397 A | 7/1998 | Koukline |
| 5,785,713 A | 7/1998 | Jobe |
| 5,788,698 A | 8/1998 | Savornin |
| 5,810,811 A | 9/1998 | Yates et al. |
| 5,823,066 A | 10/1998 | Huitema et al. |
| 5,829,662 A | 11/1998 | Allen et al. |
| 5,830,121 A | 11/1998 | Enomoto et al. |
| 5,849,023 A | 12/1998 | Mericle |
| 5,849,028 A | 12/1998 | Chen |
| 5,855,311 A | 1/1999 | Hamblin et al. |
| 5,861,005 A | 1/1999 | Kontos |
| 5,865,361 A | 2/1999 | Milliman et al. |
| 5,876,401 A | 3/1999 | Schulze et al. |
| 5,891,156 A | 4/1999 | Gessner et al. |
| 5,893,813 A | 4/1999 | Yamamoto |
| 5,895,396 A | 4/1999 | Day et al. |
| 5,906,607 A | 5/1999 | Taylor et al. |
| 5,911,721 A | 6/1999 | Nicholson et al. |
| 5,918,791 A | 7/1999 | Sorrentino et al. |
| 5,928,222 A | 7/1999 | Kleinerman |
| 5,944,717 A | 8/1999 | Lee et al. |
| 5,944,736 A | 8/1999 | Taylor et al. |
| 5,954,259 A | 9/1999 | Viola et al. |
| 5,961,521 A | 10/1999 | Roger |
| 5,964,394 A | 10/1999 | Robertson |
| 5,968,044 A | 10/1999 | Nicholson et al. |
| 5,976,171 A | 11/1999 | Taylor |
| 5,980,518 A | 11/1999 | Carr et al. |
| 5,980,548 A | 11/1999 | Evans et al. |
| 5,991,355 A | 11/1999 | Dahlke |
| 5,991,650 A | 11/1999 | Swanson et al. |
| 5,992,724 A | 11/1999 | Snyder |
| 5,997,552 A | 12/1999 | Person et al. |
| 6,004,335 A | 12/1999 | Vaitekunas et al. |
| 6,007,550 A | 12/1999 | Wang et al. |
| 6,010,054 A | 1/2000 | Johnson et al. |
| 6,013,077 A | 1/2000 | Harwin |
| 6,015,417 A | 1/2000 | Reynolds, Jr. |
| 6,017,354 A | 1/2000 | Culp et al. |
| 6,030,410 A | 2/2000 | Zurbrugg |
| 6,032,849 A | 3/2000 | Mastri et al. |
| 6,039,731 A | 3/2000 | Taylor et al. |
| 6,051,007 A | 4/2000 | Hogendijk et al. |
| 6,063,078 A | 5/2000 | Wittkampf |
| 6,063,095 A | 5/2000 | Wang et al. |
| 6,077,246 A | 6/2000 | Kullas et al. |
| 6,079,606 A | 6/2000 | Milliman et al. |
| 6,080,150 A | 6/2000 | Gough |
| 6,083,242 A | 7/2000 | Cook |
| 6,090,123 A | 7/2000 | Culp et al. |
| 6,092,422 A | 7/2000 | Binnig et al. |
| 6,109,500 A | 8/2000 | Alli et al. |
| 6,113,592 A | 9/2000 | Taylor |
| 6,123,702 A | 9/2000 | Swanson et al. |
| H1904 H | 10/2000 | Yates et al. |
| 6,126,058 A * | 10/2000 | Adams ............. A61B 17/07207 227/19 |
| 6,126,651 A | 10/2000 | Mayer |
| 6,127,811 A | 10/2000 | Shenoy et al. |
| 6,132,425 A | 10/2000 | Gough |
| 6,165,169 A | 12/2000 | Panescu et al. |
| 6,166,538 A | 12/2000 | D'Alfonso |
| 6,179,840 B1 | 1/2001 | Bowman |
| 6,187,009 B1 | 2/2001 | Herzog et al. |
| 6,187,019 B1 | 2/2001 | Stefanchik et al. |
| 6,190,401 B1 | 2/2001 | Green et al. |
| 6,193,501 B1 | 2/2001 | Masel et al. |
| 6,202,914 B1 | 3/2001 | Geiste et al. |
| 6,217,573 B1 | 4/2001 | Webster |
| 6,228,534 B1 | 5/2001 | Takeuchi et al. |
| 6,231,565 B1 | 5/2001 | Tovey et al. |
| 6,236,874 B1 | 5/2001 | Devlin et al. |
| 6,237,604 B1 | 5/2001 | Burnside et al. |
| 6,241,139 B1 | 6/2001 | Milliman et al. |
| 6,245,065 B1 | 6/2001 | Panescu et al. |
| 6,248,117 B1 | 6/2001 | Blatter |
| 6,250,532 B1 | 6/2001 | Green et al. |
| 6,258,111 B1 | 7/2001 | Ross et al. |
| 6,264,086 B1 | 7/2001 | McGuckin, Jr. |
| 6,264,087 B1 | 7/2001 | Whitman |
| 6,264,653 B1 | 7/2001 | Falwell |
| 6,281,471 B1 | 8/2001 | Smart |
| 6,288,534 B1 | 9/2001 | Starkweather et al. |
| 6,290,701 B1 | 9/2001 | Enayati |
| 6,293,943 B1 | 9/2001 | Panescu et al. |
| 6,295,330 B1 | 9/2001 | Skog et al. |
| 6,315,184 B1 | 11/2001 | Whitman |
| 6,329,778 B1 | 12/2001 | Culp et al. |
| 6,330,965 B1 | 12/2001 | Milliman et al. |
| 6,346,104 B2 | 2/2002 | Daly et al. |
| 6,355,066 B1 | 3/2002 | Kim |
| 6,364,884 B1 | 4/2002 | Bowman et al. |
| 6,387,092 B1 | 5/2002 | Burnside et al. |
| 6,388,240 B2 | 5/2002 | Schulz et al. |
| 6,402,766 B2 | 6/2002 | Bowman et al. |
| H2037 H | 7/2002 | Yates et al. |
| 6,412,279 B1 | 7/2002 | Coleman et al. |
| 6,425,903 B1 | 7/2002 | Voegele |
| 6,436,097 B1 | 8/2002 | Nardella |
| 6,436,107 B1 | 8/2002 | Wang et al. |
| 6,436,110 B2 | 8/2002 | Bowman et al. |
| 6,443,973 B1 | 9/2002 | Whitman |
| 6,447,517 B1 | 9/2002 | Bowman |
| 6,461,372 B1 | 10/2002 | Jensen et al. |
| 6,478,210 B2 * | 11/2002 | Adams ............. A61B 17/07207 227/176.1 |
| 6,497,707 B1 | 12/2002 | Bowman et al. |
| 6,505,768 B2 | 1/2003 | Whitman |
| 6,515,273 B2 | 2/2003 | Al-Ali |
| 6,524,316 B1 | 2/2003 | Nicholson et al. |
| 6,533,157 B1 | 3/2003 | Whitman |
| 6,540,751 B2 | 4/2003 | Enayati |
| 6,544,273 B1 | 4/2003 | Harari et al. |
| 6,554,852 B1 | 4/2003 | Oberlander |
| 6,562,071 B2 | 5/2003 | Jarvinen |
| 6,578,579 B2 | 6/2003 | Burnside et al. |
| 6,601,748 B2 | 8/2003 | Fung et al. |
| 6,601,749 B2 | 8/2003 | Sullivan et al. |
| 6,602,252 B2 | 8/2003 | Mollenauer |
| 6,611,793 B1 | 8/2003 | Burnside et al. |
| 6,616,821 B2 | 9/2003 | Broadley et al. |
| 6,629,986 B1 | 10/2003 | Ross et al. |
| 6,651,669 B1 | 11/2003 | Burnside |
| 6,656,177 B2 | 12/2003 | Truckai et al. |
| 6,669,073 B2 | 12/2003 | Milliman et al. |
| 6,669,705 B2 | 12/2003 | Westhaver et al. |
| 6,696,008 B2 | 2/2004 | Brandinger |
| 6,698,643 B2 | 3/2004 | Whitman |

(56) References Cited

U.S. PATENT DOCUMENTS

| | | |
|---|---|---|
| 6,699,177 B1 | 3/2004 | Wang et al. |
| 6,716,233 B1 | 4/2004 | Whitman |
| 6,736,085 B1 | 5/2004 | Esnouf |
| 6,792,390 B1 | 9/2004 | Burnside et al. |
| 6,793,652 B1 | 9/2004 | Whitman et al. |
| 6,817,508 B1 | 11/2004 | Racenet et al. |
| 6,830,174 B2 | 12/2004 | Hillstead et al. |
| 6,843,403 B2 | 1/2005 | Whitman |
| 6,846,307 B2 | 1/2005 | Whitman et al. |
| 6,846,308 B2 | 1/2005 | Whitman et al. |
| 6,846,309 B2 | 1/2005 | Whitman et al. |
| 6,849,071 B2 | 2/2005 | Whitman et al. |
| 6,861,639 B2 | 3/2005 | Al-Ali |
| 6,872,214 B2 | 3/2005 | Sonnenschein et al. |
| 6,899,538 B2 | 5/2005 | Matoba |
| 6,900,004 B2 | 5/2005 | Satake |
| 6,905,057 B2 | 6/2005 | Swayze et al. |
| 6,926,636 B2 | 8/2005 | Luper |
| 6,953,139 B2 | 10/2005 | Milliman et al. |
| 6,959,852 B2 | 11/2005 | Shelton, IV et al. |
| 6,964,363 B2 | 11/2005 | Wales et al. |
| 6,979,328 B2 | 12/2005 | Baerveldt et al. |
| 6,981,628 B2 | 1/2006 | Wales |
| 6,981,941 B2 | 1/2006 | Whitman et al. |
| 6,988,649 B2 | 1/2006 | Shelton, IV et al. |
| 7,000,819 B2 | 2/2006 | Swayze et al. |
| 7,032,798 B2 | 4/2006 | Whitman et al. |
| 7,044,353 B2 | 5/2006 | Mastri et al. |
| 7,048,687 B1 | 5/2006 | Reuss et al. |
| 7,055,731 B2 | 6/2006 | Shelton, IV et al. |
| 7,059,508 B2 | 6/2006 | Shelton, IV et al. |
| 7,077,856 B2 | 7/2006 | Whitman |
| 7,083,075 B2 | 8/2006 | Swayze et al. |
| 7,097,089 B2 | 8/2006 | Marczyk |
| 7,111,769 B2 | 9/2006 | Wales et al. |
| 7,118,564 B2 | 10/2006 | Ritchie et al. |
| 7,122,029 B2 | 10/2006 | Koop et al. |
| 7,128,253 B2 | 10/2006 | Mastri et al. |
| 7,128,254 B2 | 10/2006 | Shelton, IV et al. |
| 7,140,528 B2 | 11/2006 | Shelton, IV |
| 7,143,924 B2 | 12/2006 | Scirica et al. |
| 7,143,925 B2 | 12/2006 | Shelton, IV et al. |
| 7,143,926 B2 | 12/2006 | Shelton, IV et al. |
| 7,147,138 B2 | 12/2006 | Shelton, IV |
| 7,186,966 B2 | 3/2007 | Al-Ali |
| 7,193,519 B2 | 3/2007 | Root et al. |
| 7,217,269 B2 | 5/2007 | El-Galley et al. |
| 7,220,232 B2 | 5/2007 | Suorsa et al. |
| 7,240,817 B2 | 7/2007 | Higuchi |
| 7,241,270 B2 | 7/2007 | Horzewski et al. |
| 7,246,734 B2 | 7/2007 | Shelton, IV |
| 7,303,108 B2 | 12/2007 | Shelton, IV |
| 7,328,828 B2 | 2/2008 | Ortiz et al. |
| 7,335,169 B2 | 2/2008 | Thompson et al. |
| 7,364,061 B2 | 4/2008 | Swayze et al. |
| 7,380,695 B2 | 6/2008 | Doll et al. |
| 7,380,696 B2 | 6/2008 | Shelton, IV et al. |
| 7,404,508 B2 | 7/2008 | Smith et al. |
| 7,416,101 B2 | 8/2008 | Shelton, IV et al. |
| 7,419,080 B2 | 9/2008 | Smith et al. |
| 7,422,136 B1 | 9/2008 | Marczyk |
| 7,422,139 B2 | 9/2008 | Shelton, IV et al. |
| 7,431,188 B1 | 10/2008 | Marczyk |
| 7,431,189 B2 | 10/2008 | Shelton, IV et al. |
| 7,434,715 B2 | 10/2008 | Shelton, IV et al. |
| 7,441,684 B2 | 10/2008 | Shelton, IV et al. |
| 7,448,525 B2 | 11/2008 | Shelton, IV et al. |
| 7,461,767 B2 | 12/2008 | Viola et al. |
| 7,464,846 B2 | 12/2008 | Shelton, IV et al. |
| 7,464,847 B2 | 12/2008 | Viola et al. |
| 7,464,849 B2 | 12/2008 | Shelton, IV et al. |
| 7,481,348 B2 | 1/2009 | Marczyk |
| 7,487,899 B2 | 2/2009 | Shelton, IV et al. |
| 7,549,563 B2 | 6/2009 | Mather et al. |
| 7,552,854 B2 | 6/2009 | Wixey et al. |
| 7,556,185 B2 | 7/2009 | Viola |
| 7,568,603 B2 | 8/2009 | Shelton, IV et al. |
| 7,637,409 B2 | 12/2009 | Marczyk |
| 7,641,093 B2 | 1/2010 | Doll et al. |
| 7,644,848 B2 | 1/2010 | Swayze et al. |
| 7,648,055 B2 | 1/2010 | Marczyk |
| 7,670,334 B2 | 3/2010 | Hueil et al. |
| 7,694,809 B2 | 4/2010 | Garbini et al. |
| 7,721,931 B2 | 5/2010 | Shelton, IV et al. |
| 7,740,159 B2 | 6/2010 | Shelton, IV et al. |
| 7,753,248 B2 | 7/2010 | Viola |
| 7,757,925 B2 | 7/2010 | Viola et al. |
| 7,766,207 B2 | 8/2010 | Mather et al. |
| 7,766,210 B2 | 8/2010 | Shelton, IV et al. |
| 7,770,775 B2 | 8/2010 | Shelton, IV et al. |
| 7,784,663 B2 | 8/2010 | Shelton, IV |
| 7,815,090 B2 | 10/2010 | Marczyk |
| 7,823,760 B2 | 11/2010 | Zemlok et al. |
| 7,845,534 B2 | 12/2010 | Viola et al. |
| 7,870,989 B2 | 1/2011 | Viola et al. |
| 7,886,953 B2 | 2/2011 | Schwemberger et al. |
| 7,887,530 B2 | 2/2011 | Zemlok et al. |
| 7,905,897 B2 | 3/2011 | Whitman et al. |
| 7,909,221 B2 | 3/2011 | Viola et al. |
| 7,922,063 B2 | 4/2011 | Zemlok et al. |
| 7,931,660 B2 | 4/2011 | Aranyi et al. |
| 7,950,560 B2 | 5/2011 | Zemlok et al. |
| 7,955,352 B2 | 6/2011 | McEwen et al. |
| 3,006,885 A1 | 8/2011 | Marczyk |
| 3,006,887 A1 | 8/2011 | Marczyk |
| 3,011,551 A1 | 9/2011 | Marczyk et al. |
| 3,020,742 A1 | 9/2011 | Marczyk |
| 3,025,199 A1 | 9/2011 | Whitman et al. |
| 3,038,044 A1 | 10/2011 | Viola |
| 3,052,024 A1 | 11/2011 | Viola et al. |
| 8,066,721 B2 | 11/2011 | Kortenbach et al. |
| 8,074,858 B2 | 12/2011 | Marczyk |
| 8,092,493 B2 | 1/2012 | Marczyk |
| 8,128,645 B2 | 3/2012 | Sonnenschein et al. |
| 8,132,705 B2 | 3/2012 | Viola et al. |
| 8,157,150 B2 | 4/2012 | Viola et al. |
| 8,186,555 B2 | 5/2012 | Shelton, IV et al. |
| 8,201,721 B2 | 6/2012 | Zemlok et al. |
| 8,210,412 B2 | 7/2012 | Marczyk |
| 8,240,536 B2 | 8/2012 | Marczyk |
| 8,240,537 B2 | 8/2012 | Marczyk |
| 8,267,924 B2 | 9/2012 | Zemlok et al. |
| 8,328,823 B2 | 12/2012 | Aranyi et al. |
| 8,348,125 B2 | 1/2013 | Viola et al. |
| 2002/0103489 A1 | 8/2002 | Ku |
| 2002/0111641 A1 | 8/2002 | Peterson et al. |
| 2002/0165541 A1 | 11/2002 | Whitman |
| 2003/0090201 A1 | 5/2003 | Peng |
| 2003/0114851 A1 | 6/2003 | Truckai et al. |
| 2003/0120306 A1 | 6/2003 | Burbank et al. |
| 2004/0232201 A1 | 11/2004 | Wenchell et al. |
| 2005/0006429 A1 | 1/2005 | Wales et al. |
| 2005/0010235 A1 | 1/2005 | VanDusseldorp |
| 2005/0131390 A1 | 6/2005 | Heinrich et al. |
| 2005/0139636 A1 | 6/2005 | Schwemberger et al. |
| 2005/0177176 A1 | 8/2005 | Gerbi et al. |
| 2005/0192609 A1 | 9/2005 | Whitman et al. |
| 2005/0247753 A1 | 11/2005 | Kelly et al. |
| 2006/0000867 A1 | 1/2006 | Shelton et al. |
| 2007/0023477 A1 | 2/2007 | Whitman et al. |
| 2007/0029363 A1 | 2/2007 | Popov |
| 2007/0084897 A1 | 4/2007 | Shelton et al. |
| 2007/0102472 A1 | 5/2007 | Shelton |
| 2007/0175949 A1 | 8/2007 | Shelton et al. |
| 2007/0175950 A1 | 8/2007 | Shelton et al. |
| 2007/0175951 A1 | 8/2007 | Shelton et al. |
| 2007/0175955 A1 | 8/2007 | Shelton et al. |
| 2007/0219563 A1 | 9/2007 | Voegele |
| 2008/0029570 A1 | 2/2008 | Shelton et al. |
| 2008/0029573 A1 | 2/2008 | Shelton et al. |
| 2008/0029574 A1 | 2/2008 | Shelton et al. |
| 2008/0029575 A1 | 2/2008 | Shelton et al. |
| 2008/0135600 A1 | 6/2008 | Hiranuma et al. |
| 2008/0169329 A1 | 7/2008 | Shelton et al. |

(56) References Cited

U.S. PATENT DOCUMENTS

| | | |
|---|---|---|
| 2008/0185419 A1 | 8/2008 | Smith et al. |
| 2008/0197167 A1 | 8/2008 | Viola et al. |
| 2008/0255413 A1 | 10/2008 | Zemlok et al. |
| 2008/0255607 A1 | 10/2008 | Zemlok |
| 2009/0018624 A1 | 1/2009 | Levinson et al. |
| 2009/0090201 A1 | 4/2009 | Viola |
| 2009/0090763 A1 | 4/2009 | Zemlok et al. |
| 2010/0200636 A1 | 8/2010 | Zemlok et al. |
| 2010/0312257 A1 | 12/2010 | Aranyi |
| 2010/0320254 A1 | 12/2010 | Zemlok et al. |
| 2011/0034910 A1 | 2/2011 | Ross et al. |
| 2011/0062211 A1 | 3/2011 | Ross et al. |
| 2011/0168757 A1 | 7/2011 | Viola et al. |
| 2011/0172681 A1 | 7/2011 | Aranyi et al. |
| 2011/0190738 A1 | 8/2011 | Zemlok et al. |
| 2011/0301579 A1 | 12/2011 | Marczyk et al. |
| 2011/0303735 A1 | 12/2011 | Marczyk |
| 2012/0055972 A1 | 3/2012 | Marczyk |
| 2012/0074197 A1 | 3/2012 | Marczyk |
| 2012/0175400 A1 | 7/2012 | Viola et al. |
| 2012/0193393 A1 | 8/2012 | Viola et al. |
| 2012/0198288 A1 | 8/2012 | Njo et al. |
| 2012/0220989 A1 | 8/2012 | Zemlok et al. |
| 2012/0223121 A1 | 9/2012 | Viola et al. |
| 2012/0241494 A1 | 9/2012 | Marczyk |
| 2012/0277790 A1 | 11/2012 | Zemlok et al. |
| 2012/0298718 A1 | 11/2012 | Marczyk |
| 2012/0298720 A1 | 11/2012 | Marczyk |
| 2017/0086847 A1* | 3/2017 | DiNardo .......... A61B 17/07292 |
| 2017/0181745 A1* | 6/2017 | Penna .................. H01R 12/721 |
| 2017/0325793 A1* | 11/2017 | Cabrera ............. A61B 17/1155 |
| 2018/0132848 A1* | 5/2018 | Miller ............... A61B 17/07207 |
| 2018/0360460 A1* | 12/2018 | Mozdzierz ......... A61B 17/3476 |

FOREIGN PATENT DOCUMENTS

| | | |
|---|---|---|
| EP | 0537570 A2 | 4/1993 |
| EP | 0647431 A2 | 4/1995 |
| EP | 0738501 A1 | 10/1996 |
| EP | 0770354 A1 | 5/1997 |
| EP | 1070487 A2 | 1/2001 |
| EP | 1201196 A1 | 5/2002 |
| EP | 1658817 A1 | 5/2006 |
| EP | 1813203 A2 | 8/2007 |
| FR | 2849589 A1 | 7/2004 |
| WO | 9414129 A1 | 6/1994 |
| WO | 9729694 A1 | 8/1997 |
| WO | 9740760 A1 | 11/1997 |
| WO | 9837825 A1 | 9/1998 |
| WO | 199952489 A1 | 10/1999 |
| WO | 0234140 A2 | 5/2002 |
| WO | 03026511 A1 | 4/2003 |
| WO | 03030743 A2 | 4/2003 |
| WO | 2004032760 A2 | 4/2004 |
| WO | 2004032766 A2 | 4/2004 |
| WO | 2007030753 A2 | 3/2007 |
| WO | 2007114868 A2 | 10/2007 |
| WO | 2007118179 A2 | 10/2007 |
| WO | 2007014355 A3 | 4/2009 |
| WO | 2009143092 A1 | 11/2009 |
| WO | 2020014056 A1 | 1/2020 |

OTHER PUBLICATIONS

Detemple, P., "Microtechnology in Modem Health Care", Med Device Technol. 9(9):18-25 (1998).

Abridged Data Sheet, "DeepCover Secure Authenticator with 1-Wire SHA-256 and 512-Bit User EEPROM", Maxim Integrated Products, Inc. pp. 1-4;42; Dec. 2012.

Data Sheet "DS28E15—1—Sire SHA-256 Secure Authenticator with 512-Bit User EEPROM"; IC-ON-Line, Electronic Component Manufacturers, pp. 1-2; Aug. 2013.

Extended European Search Report dated Jun. 29, 2020 issued in corresponding EP Appln. No. 20155141.3.

* cited by examiner

PROGRAMMABLE DISTAL TILT POSITION OF END EFFECTOR FOR POWERED SURGICAL DEVICES

CROSS-REFERENCE TO RELATED APPLICATIONS

This application is a continuation of U.S. application Ser. No. 16/732,620, filed on Jan. 2, 2020, which claims the benefit of and priority to U.S. Provisional Patent Application Ser. No. 62/800,836 filed Feb. 4, 2019. The entire disclosure of each of the foregoing application is incorporated by reference herein.

BACKGROUND

1. Technical Field

The present disclosure relates to surgical devices. More specifically, the present disclosure relates to handheld electromechanical surgical systems for performing surgical procedures with differently sized end effectors.

2. Background of Related Art

One type of surgical device is a circular clamping, cutting and stapling device. Such a device may be employed in a surgical procedure to reattach rectum portions that were previously transected, or similar procedures. Conventional circular clamping, cutting, and stapling devices include a pistol or linear grip-styled structure having an elongated shaft extending therefrom and a staple cartridge supported on the distal end of the elongated shaft. In this instance, a physician may insert the loading unit portion of the circular stapling device into a rectum of a patient and maneuver the device up the colonic tract of the patient toward the transected rectum portions. The loading unit includes a cartridge assembly having a plurality of staples. Along the proximal portion of the transected colon, an anvil assembly can be purse stringed therein. Alternatively, if desired, the anvil portion can be inserted into the colon through an incision proximal to the transected colon. The anvil and cartridge assemblies are approximated toward one another and staples are ejected from the cartridge assembly toward the anvil assembly thereby forming the staples in tissue to affect an end-to-end anastomosis, and an annular knife is fired to core a portion of the clamped tissue portions. After the end-to-end anastomosis has been effected, the circular stapling device is removed from the surgical site.

A number of surgical device manufacturers have also developed proprietary powered drive systems for operating and/or manipulating the end effectors. The powered drive systems may include a powered handle assembly, which may be reusable, and a disposable end effector that is removably connected to the powered handle assembly.

Many of the existing end effectors for use with existing powered surgical devices and/or handle assemblies are driven by a linear driving force. For example, end effectors for performing endo-gastrointestinal anastomosis procedures, end-to-end anastomosis procedures and transverse anastomosis procedures, are actuated by a linear driving force. As such, these end effectors are not compatible with surgical devices and/or handle assemblies that use rotary motion.

Some of the end effectors for use with powered surgical devices are of different sized. As such the powered surgical devices interface and actuate the end effectors based on their size. Accordingly, there is a need for powered surgical devices that are programmed to operate with various end effectors taking into consideration the size and other physical attributes of the end effectors.

SUMMARY

The present disclosure provides a powered surgical device for use with an annular stapler reload and a corresponding anvil assembly. During use the anvil is approximated toward the reload to compress and form staples through the tissue. After the procedure is completed the surgical device is extracted from the patient and the anvil assembly is moved away from the reload. The present disclosure provides for a controlled extraction process by moving the anvil assembly distally for a predetermined distance such that an anvil head of the anvil assembly is tilted while the anvil assembly is still engaged to the reload, e.g., via interfacing splines on an anvil shaft and the reload. This ensures that the surgical device can be manipulated without dislodging the anvil assembly from the reload.

According to one embodiment of the present disclosure, a surgical device includes a handle assembly having a controller and a motor. The surgical device also includes an adapter assembly having: a tubular housing having a proximal end portion configured to couple to the handle assembly and a distal end portion; and an actuation assembly configured to couple to the motor. The surgical device further includes a reload configured to couple to the distal end portion of the adapter assembly; and an anvil assembly including an anvil head pivotally coupled to an anvil shaft, the anvil assembly configured to couple to the actuation assembly and the reload. The controller of the surgical device is configured to control the motor to actuate the actuation assembly to move the anvil assembly in a distal direction for a distance based on a dimension of one of the reload or the anvil head, thereby pivoting the anvil head relative to the anvil shaft while maintaining engagement of the anvil assembly to the reload.

According to one aspect of the above embodiment, the anvil assembly includes a plurality of first splines disposed on the anvil shaft and the reload includes a plurality of second splines, such that upon coupling of the anvil assembly to the reload, the plurality of first splines interface with the plurality of second splines.

According to another aspect of the above embodiment, the controller includes a memory storing a plurality of distance values. The reload includes a storage device storing a dimension value of one of the reload or the anvil head. The controller is further configured to access the storage device to read the dimension value. The controller is also configured to select one distance value from the plurality of distance values based on the dimension value and to control the motor based on the selected distance value. The distance value is equal to a radius of the anvil head.

BRIEF DESCRIPTION OF THE DRAWINGS

Embodiments of the present disclosure are described herein with reference to the accompanying drawings, wherein.

DETAILED DESCRIPTION OF EMBODIMENTS

Figure 1:
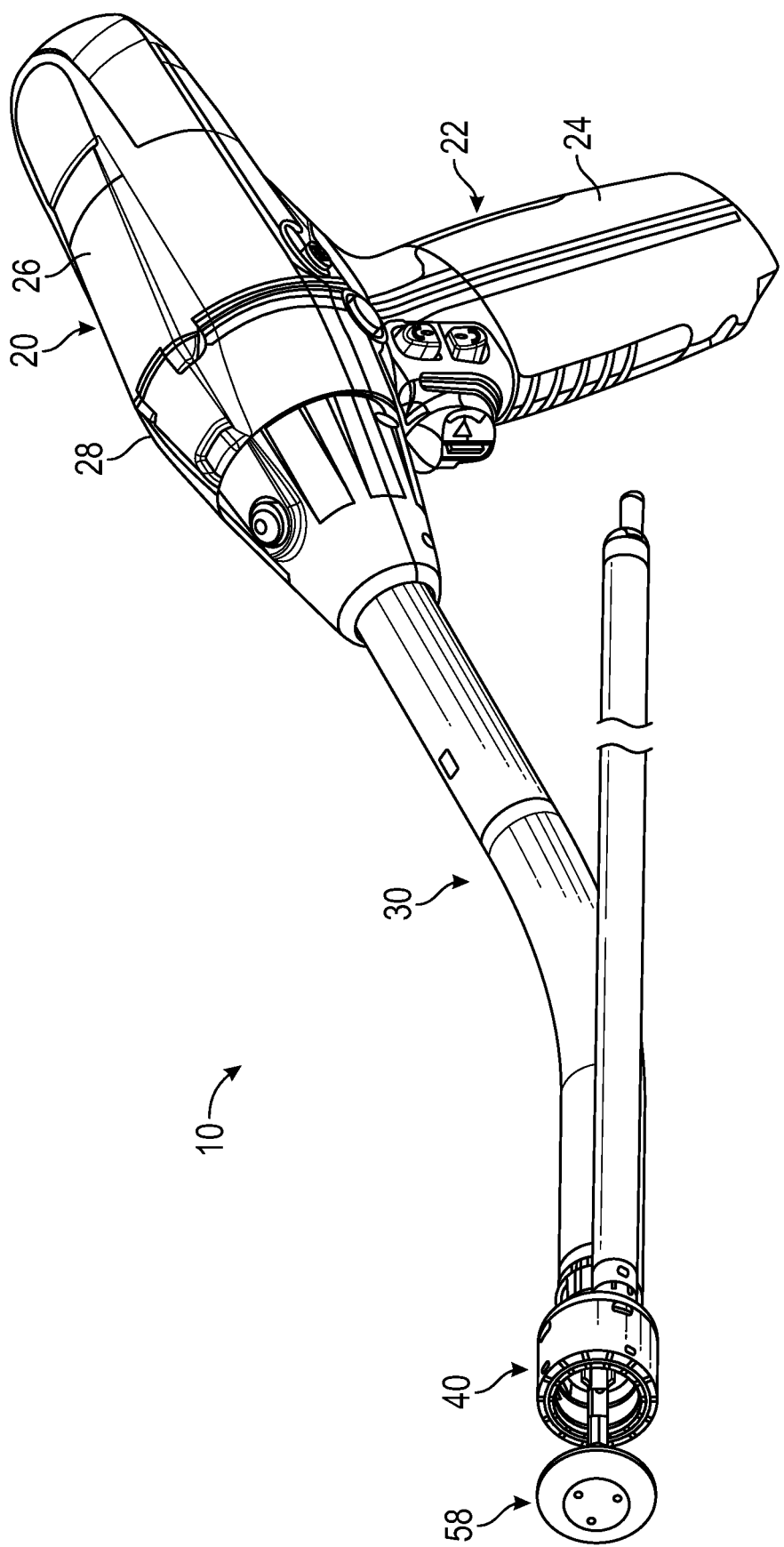
FIG. 1 is a perspective view of a handheld surgical device, an adapter assembly, an end effector having a reload and an anvil assembly according to an embodiment of the present disclosure.

Embodiments of the present disclosure are now described in detail with reference to the drawings in which like reference numerals designate identical or corresponding elements in each of the several views. As used herein, the term "clinician" refers to a doctor, a nurse or any other care provider and may include support personnel. Throughout this description, the term "proximal" will refer to the portion of the device or component thereof that is closer to the clinician and the term "distal" will refer to the portion of the device or component thereof that is farther from the clinician. Additionally, in the drawings and in the description that follows, terms such as front, rear, upper, lower, top, bottom, and similar directional terms are used simply for convenience of description and are not intended to limit the disclosure. In the following description, well-known functions or constructions are not described in detail to avoid obscuring the present disclosure in unnecessary detail.

The present disclosure relates to powered surgical devices operable with annular reloads and corresponding annular anvil assemblies. The anvil assembly includes an anvil head that is pivotable relative to an anvil shaft. This allows the anvil assembly to move from a tilted configuration during navigation of the anvil assembly within the patient and a deployed configuration in which the anvil assembly is used to clamp tissue between the reload and form staples in the tissue. The reload includes a storage device storing one or more data values describing the reload, such as dimensions (e.g., diameter). The storage device is accessible by the surgical device, which utilizes the data values to determine a distance for moving the anvil assembly during extraction. In particular, the surgical device stores a plurality of distance values in its memory and selects an appropriate distance value based on the data value from the storage device. This ensures that the surgical device moves the anvil assembly for the selected distance, which is predetermined to ensure that the anvil assembly is transitioned to a tilted configuration while being engaged to the reload.

Figure 2:
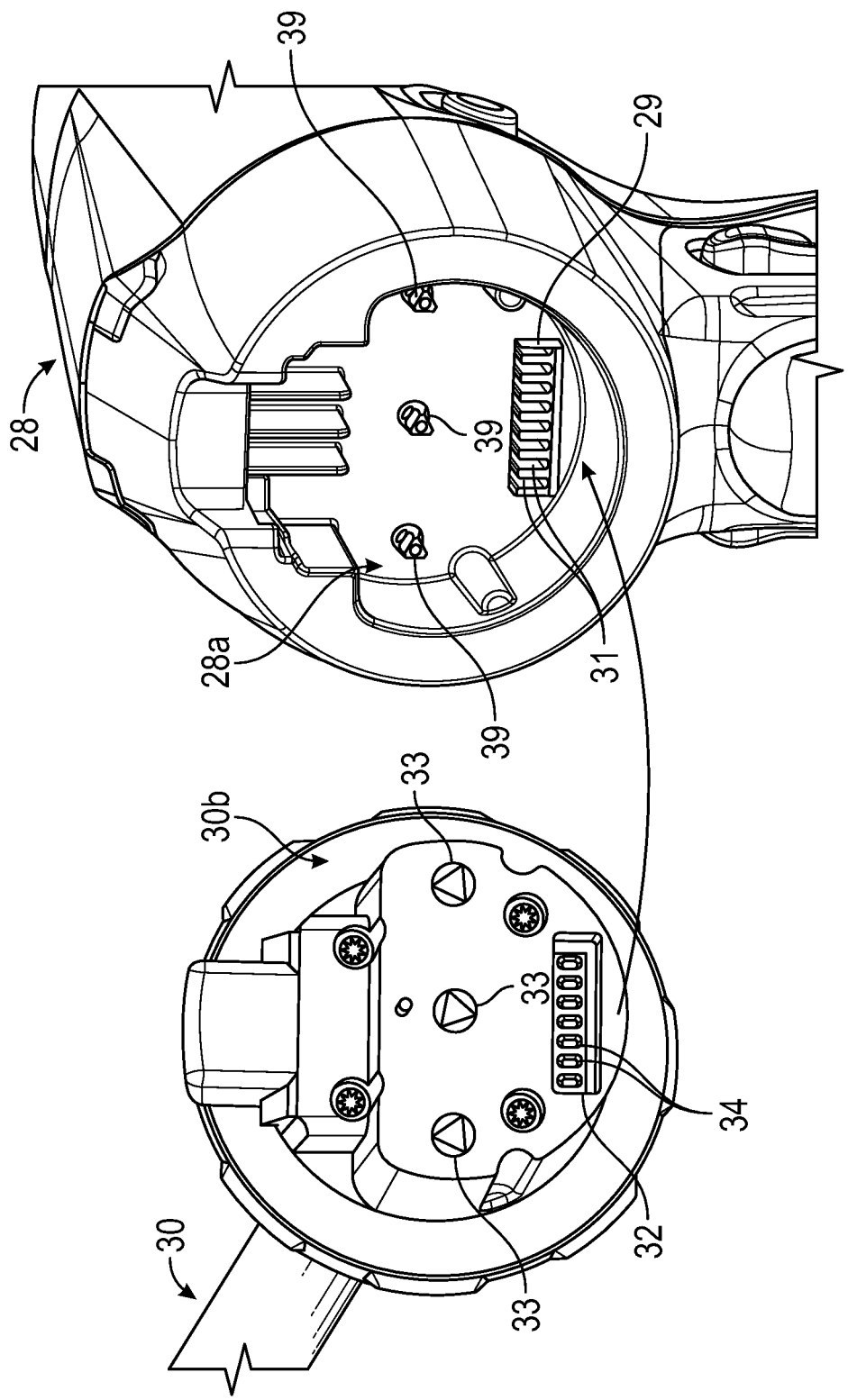
FIG. 2 is a perspective view illustrating a connection of the adapter assembly and the handle assembly of FIG. 1 according to an embodiment of the present disclosure.

With reference to FIG. 1, a powered surgical device 10 includes a handle assembly 20, which is configured for selective connection with an adapter assembly 30, which in turn, is configured for selective connection with an end effector, such as an annular reload 40. The handle assembly 20 includes a handle housing 22 having a lower housing portion 24, an intermediate housing portion 26 extending from and/or supported on a portion of the lower housing portion 24, and an upper housing portion 28 extending from and/or supported on a portion of the intermediate housing portion 26. As shown in FIG. 2, a distal portion of the upper housing portion 28 defines a nose or connecting portion 28a that is configured to accept a proximal end portion 30b of the adapter assembly 30.

Figure 3:
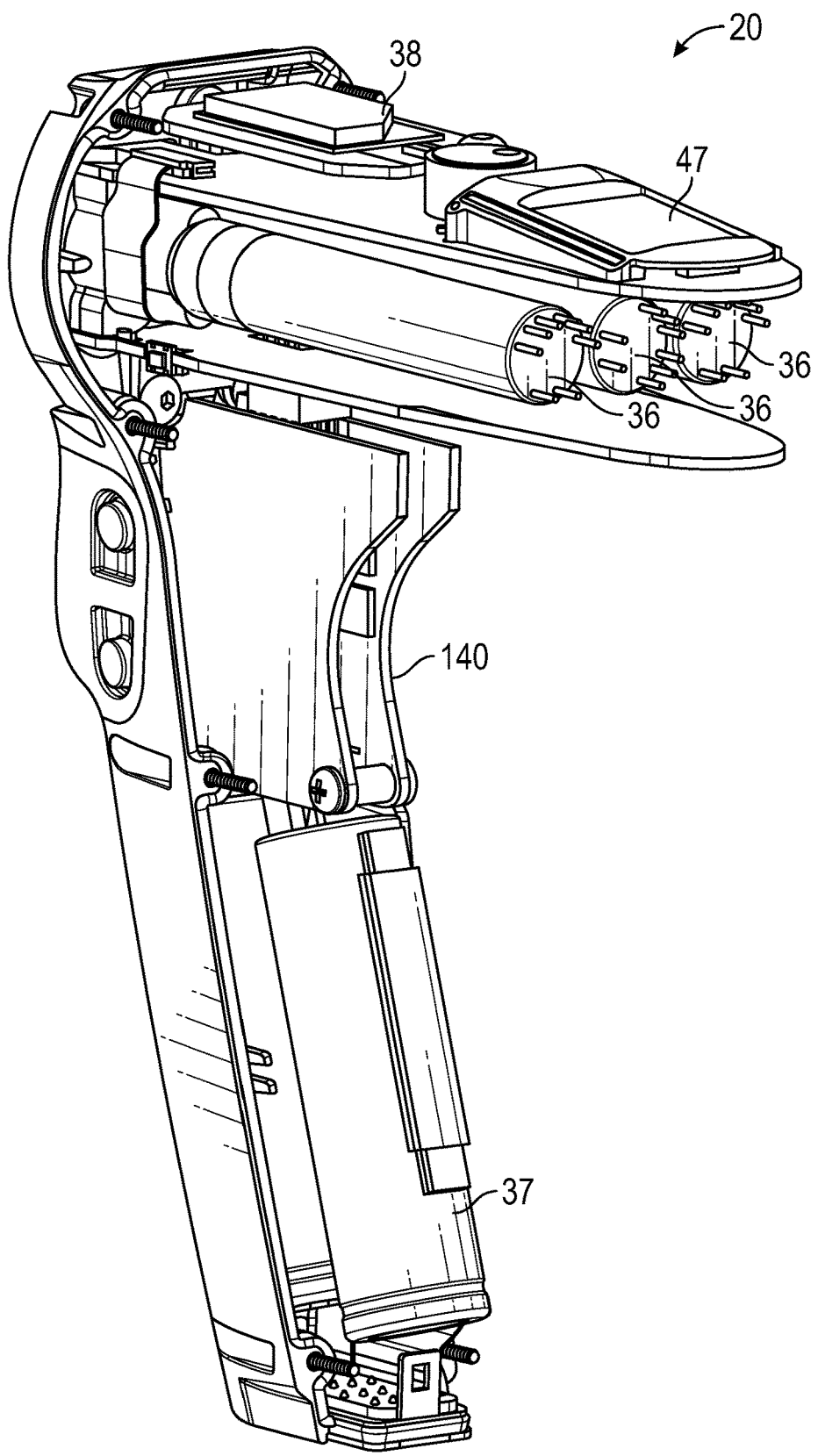
FIG. 3 is perspective view of internal components of the handle assembly according to an embodiment of the present disclosure.

With reference to FIG. 3, the handle assembly 20 includes one or more motors 36 which are coupled to a battery 37. The handle assembly 20 also includes a main controller 38 for operating the motors 36 and other electronic components of the handle assembly 20, the adapter assembly 30, and the reload 40. The main controller 38 main include any suitable logic controller (e.g., FPGA) and a memory storing software instructions executable by the logic controller to operate the motors 36 as well as other components of the surgical device 10. The memory of the main controller 38 may also store various data in addition to software instructions. The motors 36 are coupled to corresponding drive shafts 39 (FIG. 2), which are configured to engage sockets 33 on the proximal end portion 30b, such that rotation of the drive shafts 39 is imparted on the sockets 33. The actuation assembly 52 (FIG. 6B) is coupled to a respective socket 33. The actuation assembly 52 is configured to transfer rotational motion of the sockets 33 into linear motion and to actuate the reload 40 (FIG. 1) along with the anvil assembly 58.

Figure 4:
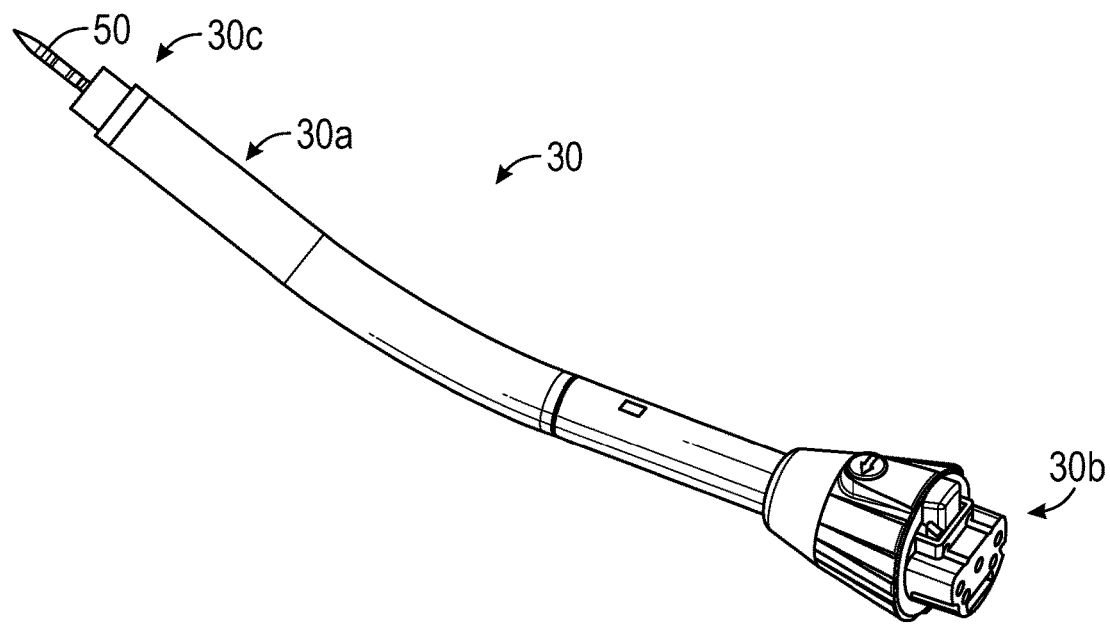
FIG. 4 is a perspective view of the adapter assembly of FIG. 1 without the reload according to an embodiment of the present disclosure.

With reference to FIG. 4, the adapter assembly 30 includes a tubular housing 30a that extends between a proximal end portion 30b that is configured for operable connection to the connecting portion 28a of the handle assembly 20 and an opposite, distal end portion 30c that is configured for operable connection to the reload 40. In this manner, the adapter assembly 30 is configured to convert a rotational motion provided by the handle assembly 20 into axial translation useful for advancing/retracting a trocar member 50 slidably disposed within the distal end portion 30c of the adapter assembly 30 (FIG. 5) for firing staples of the reload 40.

With reference to FIG. 2, the connecting portion 28a includes an electrical receptacle 29 having a plurality of electrical contacts 31, which are in electrical communication with electronic (e.g., main controller 38) and electrical components (e.g., battery 37) of the handle assembly 20. The adapter assembly 30 includes a counterpart electrical connector 32 supported within the proximal end portion 30b that is configured to engage the electrical receptacle 29. The electrical connector 32 also includes a plurality of electrical contacts 34 that engage and electrically connect to their counterpart electrical contacts 31. Electrical connector 32 is of the adapter assembly 30.

With reference to FIG. 4, the trocar member 50 is slidably disposed within the tubular housing 30a of the adapter assembly 30 and extends past the distal end portion 30c thereof. In this manner, the trocar member 50 is configured for axial translation, which in turn, causes a corresponding axial translation of an anvil assembly 58 (FIG. 1) of the reload 40 to fire the staples (not shown) disposed therein. The trocar member 50 includes a proximal end which is coupled to the tubular housing 30a of the adapter assembly 30. A distal end portion of the trocar member 50 is configured to selectively engage the anvil assembly 58 of the reload 40 (FIG. 4). In this manner, when the anvil assembly 58 is connected to the trocar member 50, as will be described in detail hereinbelow, axial translation of the trocar member 50 in the first direction results in an opening of the anvil assembly 58 relative to the reload 40, and axial translation of the trocar member 50 in a second, opposite direction, results in a closing of the anvil assembly 58 relative to the reload 40.

Figure 5:
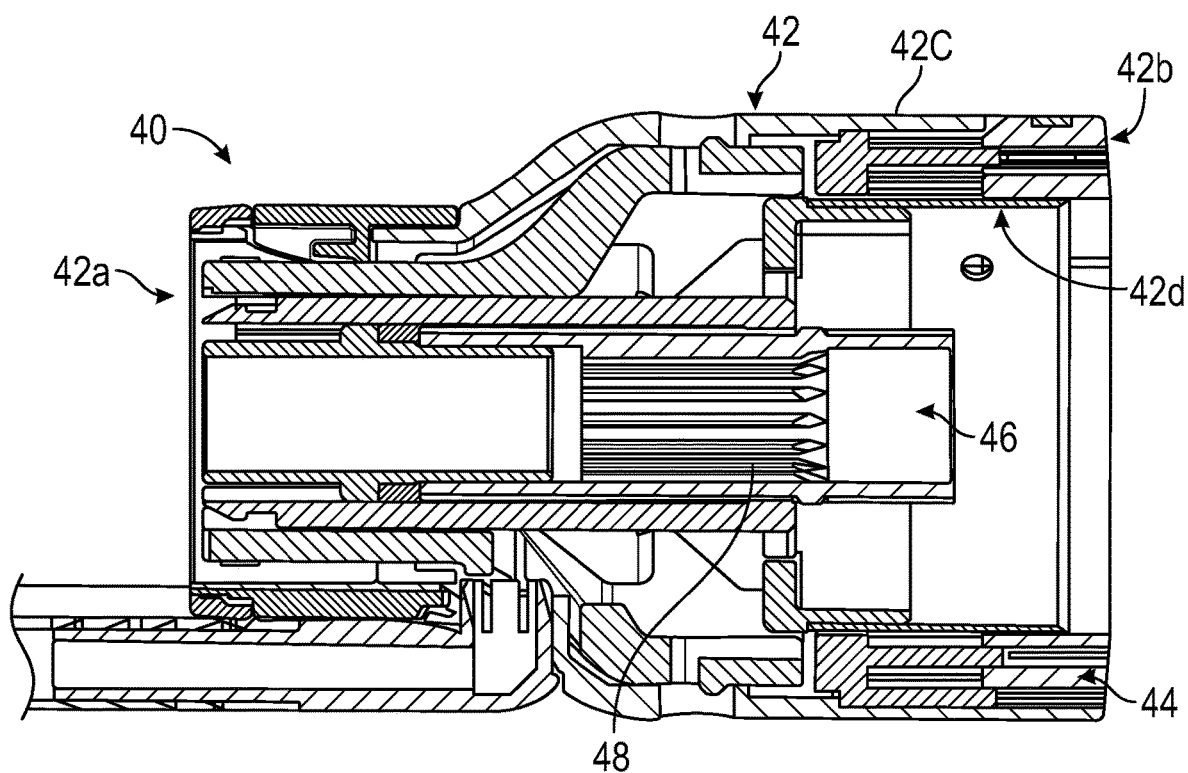
FIG. 5 is a side, cross-sectional view, of the reload of FIG. 1 according to an embodiment of the present disclosure.

As illustrated in FIGS. 1 and 5, the reload 40 is configured for operable connection to adapter assembly 30 and is configured to fire and form an annular array of surgical staples, and to sever a ring of tissue. The reload 40 includes a housing 42 having a proximal end portion 42a and a distal end portion 42b and a staple cartridge 44 fixedly secured to the distal end portion 42b of the housing 42. The proximal end portion 42a of the housing 42 is configured for selective connection to the distal end portion 30c of the adapter assembly 30 and includes a means for ensuring the reload 40 is radially aligned or clocked relative to the adapter assembly 30.

With reference to FIG. 5, the housing 42 of the reload 40 includes an outer cylindrical portion 42c and an inner cylindrical portion 42d. The outer cylindrical portion 42c and the inner cylindrical portion 42d of the reload 40 are coaxial and define a recess 46. The recess 46 of the reload 40 includes a plurality of longitudinally extending ridges or splines 48 projecting from an inner surface thereof which is configured to radially align the anvil assembly 58 relative to the reload 40 during a stapling procedure.

The reload 40 also includes a storage device 41 may be any non-volatile storage medium (e.g., EEPROM) that is configured to store any data pertaining to the reload 40, including but not limited to, usage count, identification information, model number, serial number, staple size, stroke length, maximum actuation force, minimum actuation force, factory calibration data, and the like. In embodiments, the data may be encrypted and is only decryptable by the main controller 38 having appropriate keys. The data may also be used to authenticate the reload 40. The storage device 41 may be configured in read only or read/write modes, allowing the main controller 38 to read as well as write data onto the storage device 41.

Figure 6A:
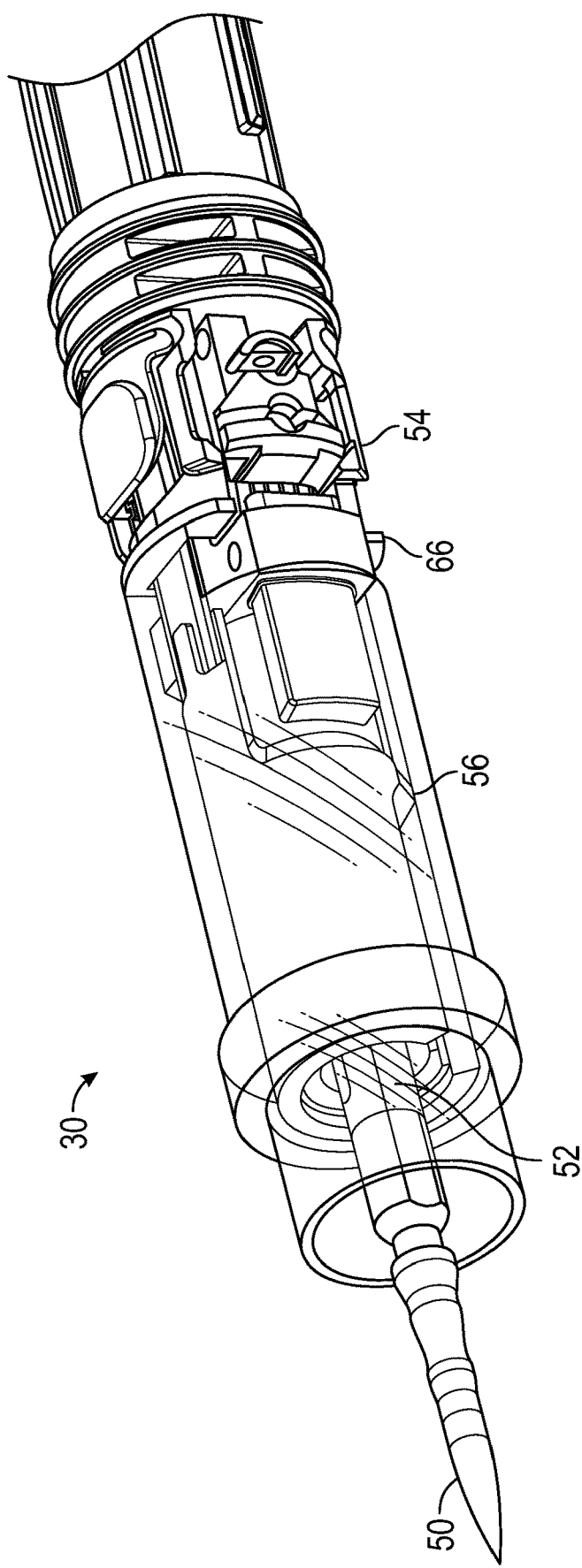
FIG. 6A is a perspective view of the distal end portion of the adapter assembly according to an embodiment of the present disclosure.
Figure 6B:
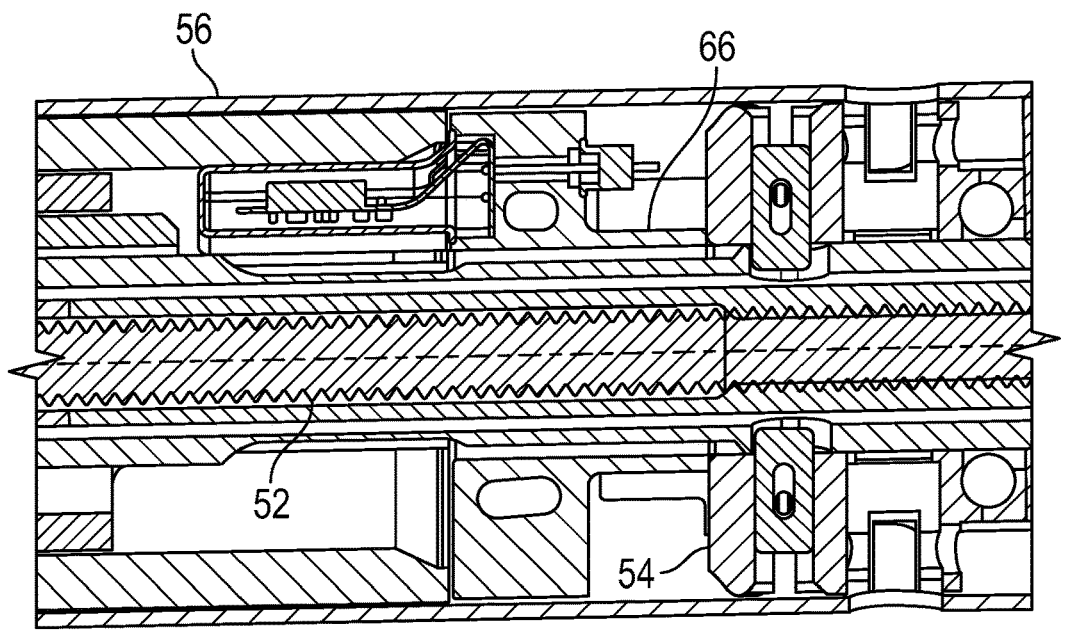
FIG. 6B is a cross-sectional view of the distal end portion of the adapter assembly according to an embodiment of the present disclosure.
Figure 7:
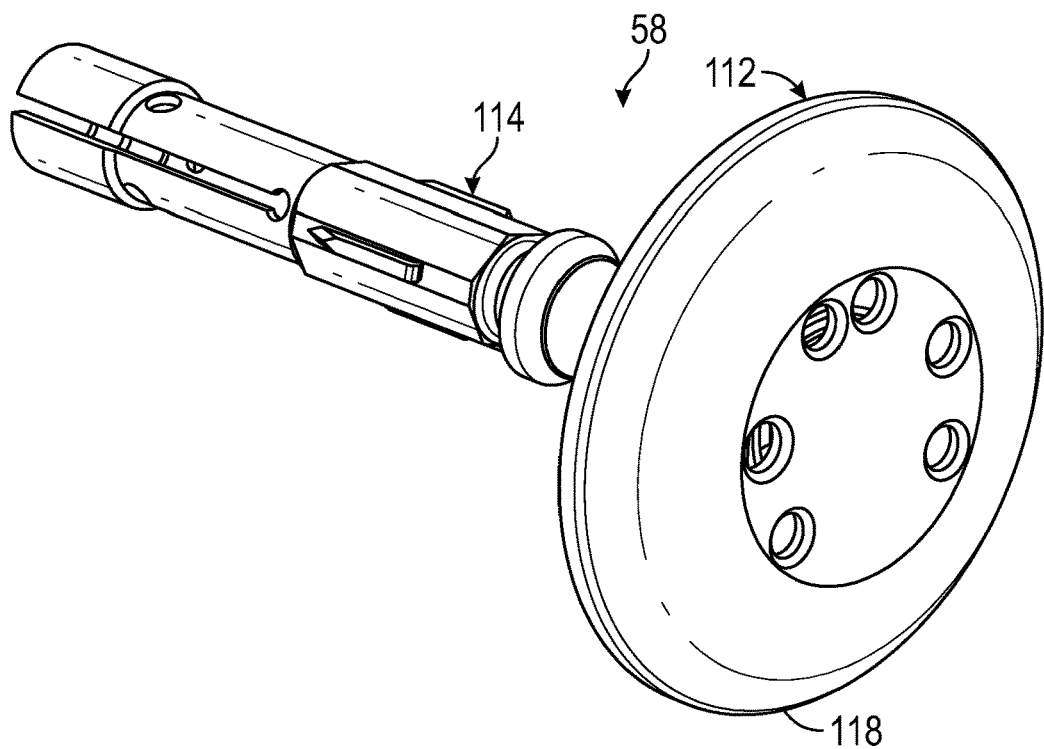
FIG. 7 is a front, perspective view of an anvil assembly according to the present disclosure.

Load sensing assembly 66 is electrically connected to electrical connector 32 via a wiring harness. As shown in FIGS. 6A and 6B, an actuation assembly 52, which is coupled to the trocar member 50, extends through the load sensing assembly 66. The load sensing assembly 66 provides strain measurements imparted on the adapter assembly 30 during movement of the trocar member 50 when coupled to the anvil assembly 58 during clamping, stapling, cutting, and other mechanical actuations. The load sensing assembly 66 is disposed between a support block 54 and a connector sleeve 56. During operation of the surgical device 10, namely, clamping, stapling, and cutting, load sensing assembly 66 is elastically deformed (similar to a support beam) in proportion to the forces applied to the support block 54 and the connector sleeve 56. A change in a baseline of the measurement signal is indicative of the forces being imparted on the support block 54 and the connector sleeve 56, which are generally descriptive of the forces encountered during clamping, stapling, and cutting.

Figure 8:
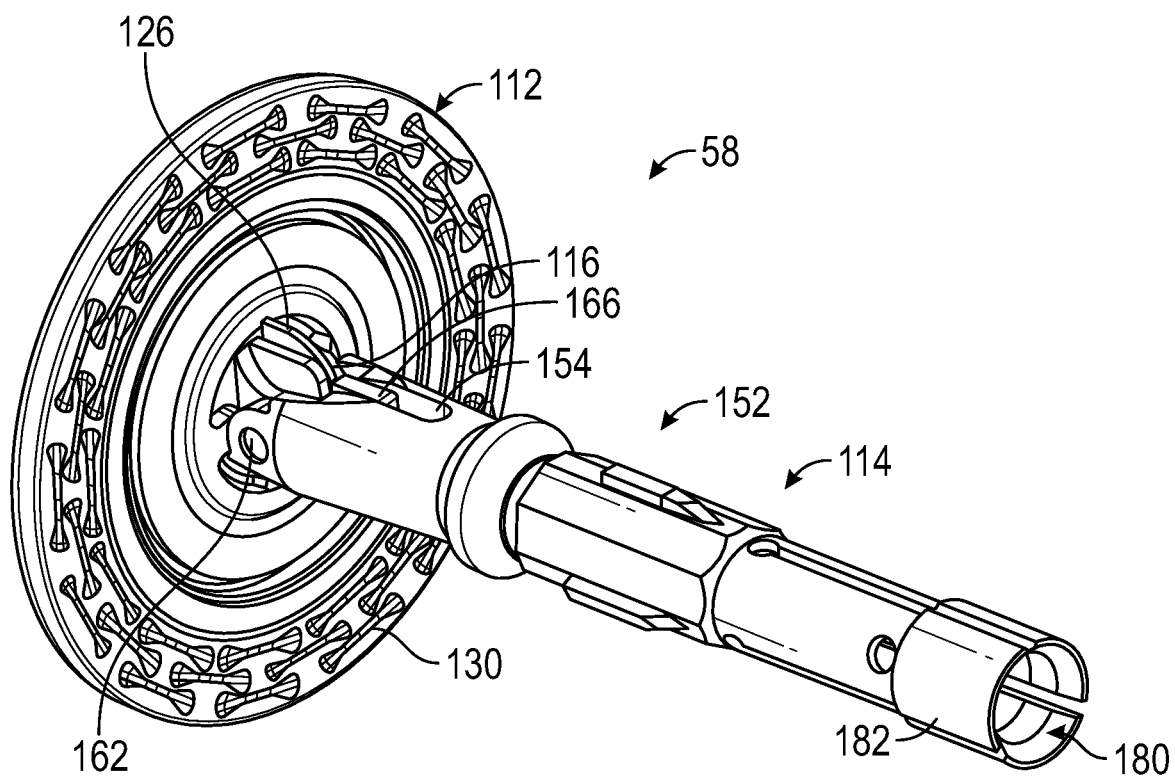
FIG. 8 is a rear, perspective view of the anvil assembly of FIG. 5.
Figure 9:
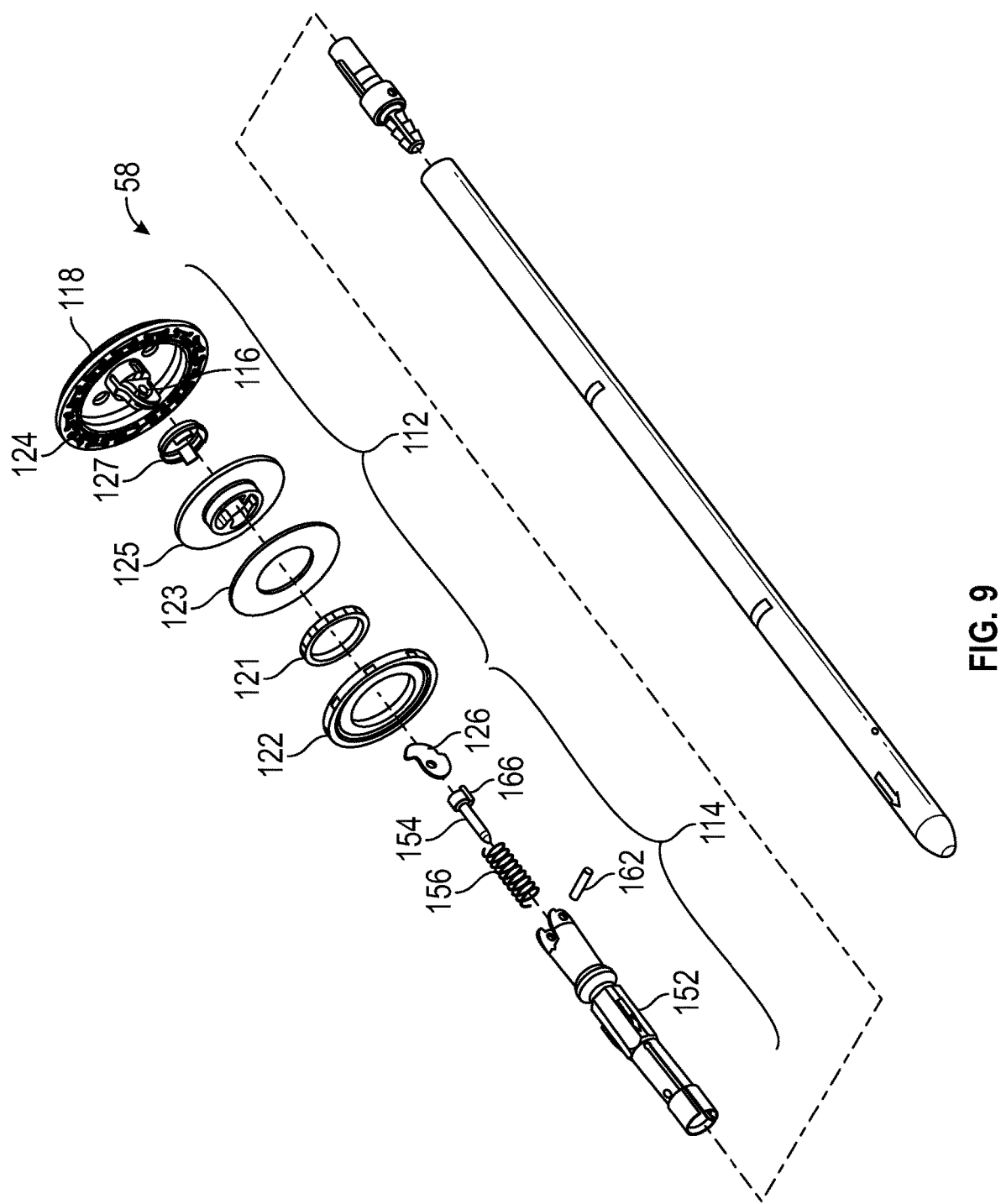
FIG. 9 is a perspective view, with parts separated, of the anvil assembly of FIG. 5.

Referring now to FIGS. 7-10, an anvil assembly 58 is provided and is configured for selective connection to trocar member 50 of adapter assembly 30 and for clamping, stapling, and cutting tissue in cooperation with reload 40. Anvil assembly 58 includes a head assembly 112 and a center rod assembly 114. As shown in FIG. 9, the head assembly 112 includes a post 116, a housing 118, a cutting ring 122, a cutting ring cover 123, an anvil plate 124, a spacer 121, a cam latch 126, and a retainer member 127. Post 116 is centrally positioned within housing 118.

The anvil plate 124 is supported in an outer annular recess of housing 118 and includes a plurality of staple pockets 130 formed therein and configured to receive and form staples. Cutting ring 122 includes a central opening which is positioned about post 116 within an inner annular recess of housing 118 between post 116 and outer annular recess. Cutting ring 122 may be formed from any thermoplastic material, such as polyethylene. Cutting ring cover 123 is secured to an outwardly facing or proximal surface of cutting ring 122.

Retainer member 127 is positioned in the inner annular recess between cutting ring 122 and a back wall of housing 118. Retainer member 127 is annular and includes a plurality of deformable tabs which engage a rear surface of cutting ring 122. Retainer member 127 prevents cutting ring 122 from moving or being pushed into the inner annular recess of housing 118 until a predetermined force sufficient to deform the tabs has been applied to cutting ring 122. When the predetermined force is reached, e.g., during cutting of tissue, cutting ring 122 is urged into the inner annular recess 136 and compresses the retainer members.

With reference to FIG. 9, anvil center rod assembly 114 includes a center rod 152, a plunger 154 and a plunger spring 156. A first end of center rod 152 includes a pair of arms 119 which define a cavity 119a. A pivot pin 162 is provided to pivotally secure post 116 to center rod 152 such that anvil head assembly 112 is pivotally mounted to anvil center rod assembly 114.

Cam latch 126 is pivotally mounted within a transverse slot of post 116 of housing 118 and about pivot pin 162. Cam latch 126 has an outer cam profile which permits plunger 154 to move forward as cam latch 126 rotates in a distal direction, and permits plunger 154 to be retracted as cam latch rotates in a proximal direction.

Plunger 154 is slidably positioned in a bore formed in the first end of center rod 152. Plunger 154 includes an engagement finger which is offset from the pivot axis of anvil head assembly 112 and biased into engagement with an edge of cam latch 126. Engagement of the finger of plunger 154 with the edge of cam latch 126 presses a leading portion of the edge of cam latch 126 against an inner periphery of cutting ring 122 to urge anvil head assembly 112 to an operative or non-tilted configuration on center rod 152.

Anvil head assembly 112 may be tilted relative to anvil center rod assembly 114 in a pre-fired tilted configuration. Tilting of anvil head assembly 112 relative to anvil center rod assembly 114 causes the body portion of cam latch 126 to engage a finger 166 of plunger 154. As cam latch 126 rotates with the tilting of anvil head assembly 112, plunger 154 is retracted with the bore of anvil center rod assembly 114, thereby compressing spring 156. In this manner, finger 166 of plunger 154 is distally biased against the body portion of cam latch 126.

Figure 10:
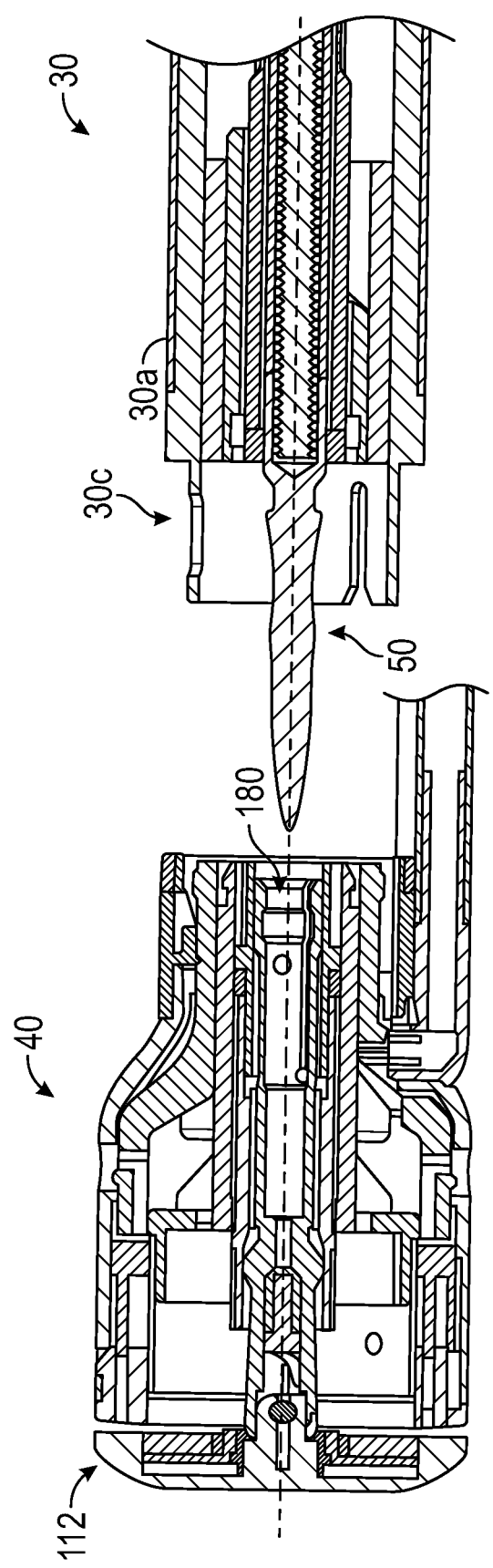
FIG. 10 is a longitudinal, cross-sectional view, illustrating the reload of FIG. 5 aligned with and separated from the distal end portion of the adapter assembly of FIG. 1.

With reference to FIGS. 8 and 9, a second end of center rod 152 includes a bore 180 defined by a plurality of flexible arms 182. The proximal end of each of the flexible arms 182 includes an internal shoulder dimensioned to releasably engage a shoulder of trocar member 50 of adapter assembly 30 to secure anvil assembly 58 to adapter assembly 30 as shown in FIG. 10. A plurality of splines 186 are formed about center rod 152. Splines 186 align the anvil assembly 58 with the reload 40 by engaging the splines 48 of the staple cartridge 44.

For a detailed description of an exemplary powered surgical stapler including an adapter assembly and a reload, reference may be made to commonly owned U.S. Patent Application Publication No. 2016/0310134 to Contini et al., titled "Handheld Electromechanical Surgical System," filed Apr. 12, 2016, incorporated in its entirety by reference hereinabove.

The anvil assembly 58 along with the reload 40 are used to staple and subsequently cut tissue, such as during anastomosis procedures. After the stapling and cutting sequences are complete, the user begins an unclamping sequence to release the anvil assembly 58 from the trocar member 50, e.g., by pressing on a control button on the handle assembly 20. The trocar member 50 is automatically extended distally, thereby moving the anvil assembly 58 away from the reload 40 and unclamping the tissue to a preset anvil tilt distance. The unclamping sequence may be illustrated on a display screen 47 (FIG. 3). In particular, an unclamping animation shows the anvil assembly 58 moving distally and the head assembly 112 being tilted. In addition, the display screen 47 may also show a lock icon to show that the anvil assembly 58 is secured to the trocar member 50. Once the anvil assembly 58 is moved away from reload 40 to its tilt distance, the display screen 47 shows the anvil assembly 58 in the extended state with the head assembly 112 in the tilted state. This indicates that the user may remove the adapter assembly 30 from the patient.

The adapter assembly 30 may be used with a variety of differently sized reloads 40. In embodiments, the reloads 40 may have a diameter from about 20 millimeters (mm) to about 40 mm. The reloads 40 may be chosen based on the thickness of the organ being resected. Additionally, the anvil assemblies 58 correspond in size to the reloads 40 being used in the procedure such that the staples of the reload 40 contact the staple pockets 130 of the anvil assembly 58. Due to the size difference of different anvil assemblies 58 the surgical device 10 advances the anvil assembly 58 to a preset anvil tilt distance based on the dimensions of the anvil assembly 58. Since the dimensions of the anvil assembly 58, such as its diameter and/or radius, correspond to the dimensions of the reload 40, the surgical device 10 obtains the dimensions data from the storage device 41. Thus, rather than moving all of the anvil assemblies 58 to the same anvil tilt distance, the surgical device 10 moves the anvil assemblies 58 to a predetermined tilt distance based on the dimensions of the reload 40. This ensures the splines 186 of the anvil assembly 58 continue to engage the splines 48 of the staple cartridge 44.

Figure 11:
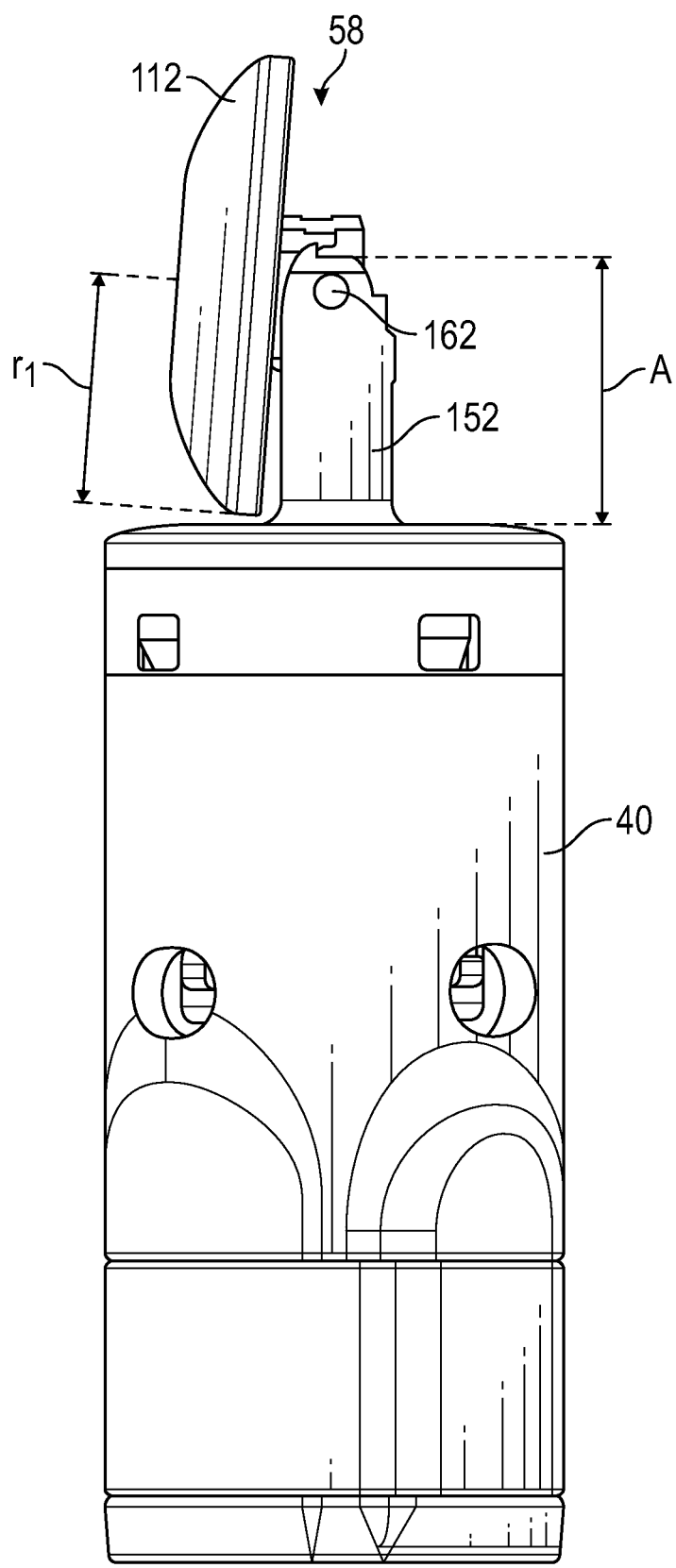
FIG. 11 is a side view of the distal end portion of the adapter assembly with the reload and a first anvil assembly in a tilted configuration according to an embodiment of the present disclosure.
Figure 12:
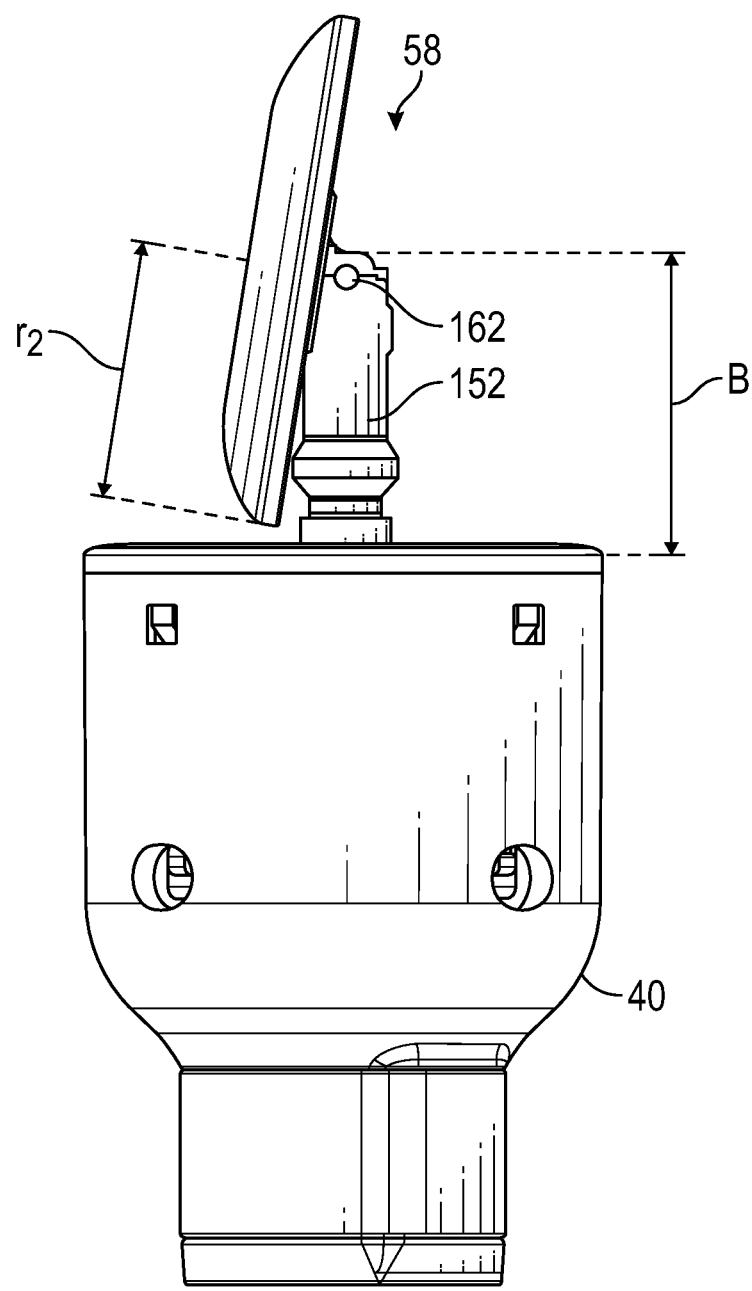
FIG. 12 is a side view of the distal end portion of the adapter assembly with the reload and a second anvil assembly in a tilted configuration according to an embodiment of the present disclosure.

With reference to FIGS. 11 and 12, the anvil assembly 158 is illustrated in a tilted configuration. FIG. 11 illustrates a smaller reload 40 (e.g., about 21 mm) whereas FIG. 12 illustrates a larger reload 40 (e.g., about 33 mm). Each of the anvil assemblies 158 is extended to a predetermined distance that corresponds to the size of the anvil assembly 158, namely its diameter and/or radius. As shown in FIGS. 11 and 12, the anvil assembly 158 of FIG. 11 is extended for a distance a and the anvil assembly 158 of FIG. 12 is extended for a distance b, based on the respective radii $r_1$ and $r_2$ of the anvil assemblies 158.

The main controller 38 of the surgical device 10 is configured to access dimensions data stored on the storage device 41 of the reload 40. The main controller 38 also stores a plurality of tilt distances in its memory. The main controller 38 is configured to select one tilt distance from the plurality of tilt distances based on the dimensions of the reload 40 and correspondingly the anvil assembly 58 as read from the storage device 41. The main controller 38 then operates the actuation assembly 52 to move the anvil assembly 58 to the selected tilt distance until the anvil head assembly 112 is tilted, allowing for extraction of the surgical device 10.

By remaining engaged to the splines 48 of the staple cartridge 44, the anvil assembly 58 is prevented from rotation in response to rotation of the surgical device 10, such as during twisting of the surgical device 10 by the clinician to pull through the anastomosis. Being able to twist the surgical device 10 allows for the anvil assembly 58 to be pulled through the anastomosis in potential snagging situations. Conversely, when the anvil assembly 58 is unsecured, it is free to spin and may remain snagged in the same position regardless of the twisting or maneuvering of the surgical device 10. Ensuring that the anvil assembly 58 remains secured may be beneficial in bariatric procedures as the tissues and locations that the anvil assemblies 58 are maneuvered in tend to move with the reload 40 rather than allowing the anvil assembly 58 to slide through the anastomosis. In these situations, twisting of the surgical device 10 allows for easier removal due to the anvil assembly 58 being engaged with the reload 40 due to the tailored anvil tilt distance that is programmed for each of the different reload sizes. Another benefit is the tailored distance shortens time required for operating the surgical device 10.

It will be understood that various modifications may be made to the embodiments of the presently disclosed adapter assemblies. Therefore, the above description should not be construed as limiting, but merely as exemplifications of embodiments. Those skilled in the art will envision other modifications within the scope and spirit of the present disclosure.

What is claimed is:
1. A surgical device including:
a handle assembly including a controller, a memory storing a plurality of tilt distances, and a motor;
a tubular housing having a proximal end portion configured to couple to the handle assembly and a distal end portion; and
an actuation assembly disposed within the tubular housing and configured to couple to the motor;
an anvil assembly including an anvil head pivotally coupled to an anvil shaft, the anvil assembly configured to couple to the actuation assembly; and
a reload configured to couple to the distal end portion of the tubular housing, the reload including a storage device storing dimension data pertaining to one of the reload or the anvil head;
wherein the controller is configured to:
access the storage device to read the dimension data;
select one tilt distance from the plurality of tilt distances based on the dimension data; and
control the motor to actuate the actuation assembly to move the anvil assembly in a distal direction for the selected tilt distance that is sufficient for the anvil head to pivot relative to the anvil shaft.

2. The surgical device according to claim 1, wherein the anvil assembly includes a plurality of first splines disposed on the anvil shaft and the reload includes a plurality of second splines.

3. The surgical device according to claim 2, wherein upon coupling of the anvil assembly to the reload, the plurality of first splines interface with the plurality of second splines.

4. The surgical device according to claim 1, wherein the dimension data includes a radius of one of the reload or the anvil head.

5. The surgical device according to claim 4, wherein the controller is configured to access the storage device to read the radius.

6. The surgical device according to claim 5, wherein the controller is configured to select one distance value from the plurality of distance values based on the radius.

7. A surgical device including:
- a tubular housing having a proximal end portion and a distal end portion and an actuation assembly;
- an anvil assembly including an anvil head pivotally coupled to an anvil shaft, the anvil assembly configured to couple to the actuation assembly;
- a reload configured to couple to the distal end portion of the tubular housing, the reload including a storage device storing a dimension data pertaining to one of the reload or the anvil head; and
- a handle assembly configured to couple to the proximal end portion of the tubular housing, the handle assembly including:
  - a motor configured to move to the actuation assembly;
  - a memory storing a plurality of tilt distances; and
  - a controller configured to:
    - access the storage device to read the dimension data;
    - select one tilt distance from the plurality of tilt distances based on the dimension data; and
    - control the motor to actuate the actuation assembly to move the anvil assembly in a distal direction for the selected tilt distance, thereby pivoting the anvil head relative to the anvil shaft.

8. The surgical device according to claim 7, wherein the anvil assembly includes a plurality of first splines disposed on the anvil shaft and the reload includes a plurality of second splines.

9. The surgical device according to claim 8, wherein upon coupling of the anvil assembly to the reload, the plurality of first splines interface with the plurality of second splines.

10. A method for controlling a surgical device, the method comprising:
- accessing a storage device of a reload, the storage device storing a dimension data pertaining to one of the reload or an anvil head;
- selecting one tilt distance from a plurality of tilt distances stored in a memory based on the dimension data;
- controlling a motor to move an actuation assembly coupled to an anvil assembly including an anvil head pivotally coupled to an anvil shaft; and
- moving the anvil assembly in a distal direction for the selected tilt distance, thereby pivoting the anvil head relative to the anvil shaft.

* * * * *